United States Patent
Turunen et al.

(10) Patent No.: US 6,892,589 B2
(45) Date of Patent: May 17, 2005

(54) PROOF TESTING METHOD AND APPARATUS FOR OPTICAL FIBRES

(75) Inventors: Harri Turunen, Helsinki (FI); Keijo Mäkelä, Espoo (FI)

(73) Assignee: Nextrom Holding S.A., Morges (CH)

( * ) Notice: Subject to any disclaimer, the term of this patent is extended or adjusted under 35 U.S.C. 154(b) by 0 days.

(21) Appl. No.: 10/380,509

(22) PCT Filed: Oct. 23, 2001

(86) PCT No.: PCT/FI01/00916

§ 371 (c)(1),
(2), (4) Date: Mar. 14, 2003

(87) PCT Pub. No.: WO02/35210

PCT Pub. Date: May 2, 2002

(65) Prior Publication Data

US 2003/0167855 A1 Sep. 11, 2003

(30) Foreign Application Priority Data

Oct. 24, 2000 (FI) .............................................. 20002333

(51) Int. Cl.⁷ ............................. G01L 5/04; G01N 3/00; B65H 67/048
(52) U.S. Cl. .................... 73/862.44; 73/839; 242/474.7
(58) Field of Search ....................... 73/862.44, 862.393, 73/862.194, 862.391, 862.452, 862.392, 800, 826–830, 834–835, 839, 858; 242/615.3, 18

(56) References Cited

U.S. PATENT DOCUMENTS

| | | | |
|---|---|---|---|
| 4,148,218 A | * 4/1979 | Knowles et al. ............... | 73/829 |
| 4,601,208 A | 7/1986 | McKay et al. | |
| 4,618,104 A | * 10/1986 | Harris ...................... | 242/476.1 |
| 5,076,104 A | * 12/1991 | Glaesemann et al. ......... | 73/830 |
| 5,322,228 A | * 6/1994 | Nagayama et al. ...... | 242/476.6 |
| 5,596,901 A | * 1/1997 | Gloor .......................... | 73/830 |
| 5,964,431 A | * 10/1999 | Chang et al. ............. | 242/615.3 |
| 6,027,062 A | 2/2000 | Bacon et al. | |
| 6,152,399 A | * 11/2000 | Chang et al. ............. | 242/615.3 |
| 6,612,189 B1 | * 9/2003 | Miyauchi ............... | 73/862.392 |

FOREIGN PATENT DOCUMENTS

EP      0 514 858 A2    11/1992
JP      A 6-129967      5/1994

* cited by examiner

Primary Examiner—Edward Lefkowitz
Assistant Examiner—Takisha Miller
(74) Attorney, Agent, or Firm—Oliff & Berridge, PLC

(57) ABSTRACT

The invention relates to a proof testing method and a proof testing apparatus for optical fibre where a fibre (1) is guided to a first pulling device (2) and further to a second pulling device (3) and then onto a reel (11, 12), whereby the pulling devices subject the fibre to a desired amount of tensile strength, as a result of which the fibre breaks if the fibre (1) strength is insufficient. To achieve a continuous pulling and proof testing process, the fibre end is guided in the case of a fibre break between the first and the second pulling device (2, 3) by means of a first channel section (5), which guides the fibre to the second pulling device (3). After the second pulling device (3) the fibre end is guided into a second channel section (8) which is off the normal fibre track and along which the fibre (1) is guided into a scrap fibre processing system. At a desired moment the fibre (1) is guided from the second channel section (8) to the normal track, along which the fibre is guided onto a reel (11, 12).

16 Claims, 3 Drawing Sheets

Figure 1:
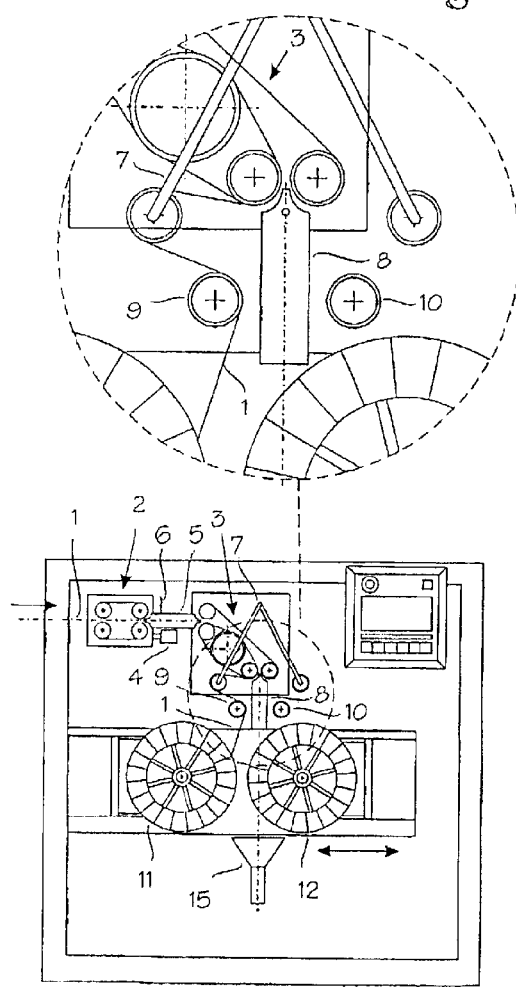

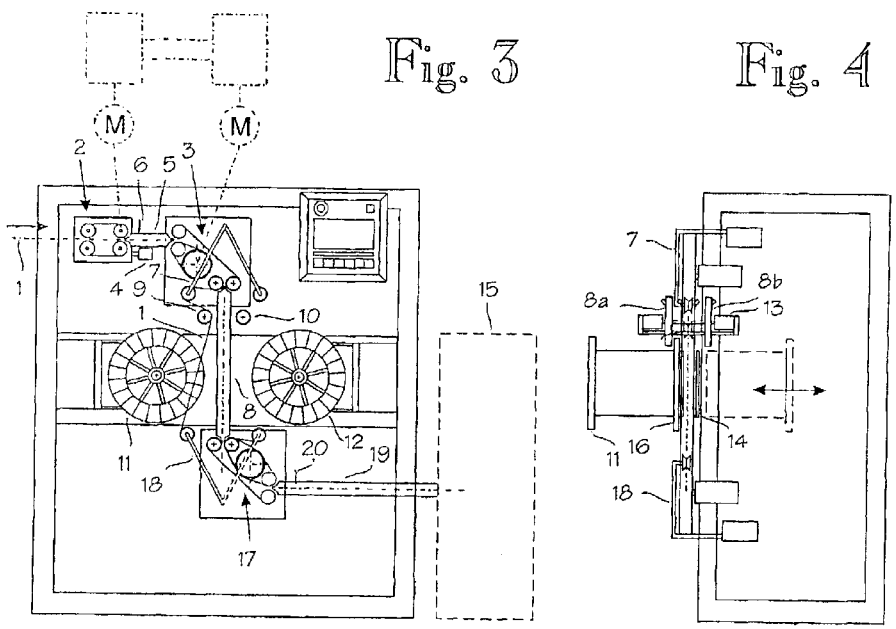
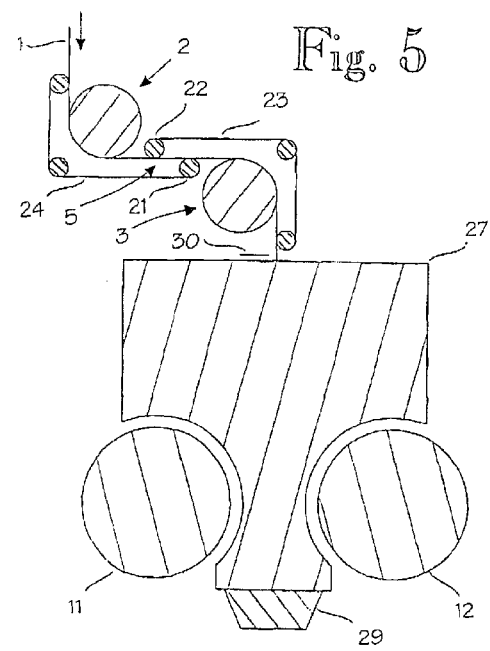

PROOF TESTING METHOD AND APPARATUS FOR OPTICAL FIBRES

The invention relates to a proof testing method for optical fibre where a fibre is guided to a first pulling device and further to a second pulling device and then onto a reel, whereby the pulling devices subject the fibre to a desired amount of tensile stress, as a result of which the fibre breaks if the fibre strength is insufficient. The invention also relates to a proof testing apparatus for optical fibres.

In the manufacture of optical fibres, a preform is first produced from a desired material and when the fibre is drawn, the preform is heated to soften it. A thin fibre is drawn from one end of the heated preform and led to a winding station, where the fibre is wound onto a reel. Before winding the fibre is coated with a protective layer and optionally with a powder so that the fibre can move easily with respect to the elements used to support the optical cable during its manufacture.

Fibre production also includes a testing phase to ensure that the fibres meet the requirements set on them by cable production. One of the most important tests conducted on fibres is the proof test, also known as a pulling test. The purpose of the proof test is to ensure that the fibre sustains the tensile stress to which is may be subjected during cable production or cable installation. The proof test is conducted e.g. by simply pulling the fibre during its manufacture with a pulling device, which applies a predetermined amount of tensile stress to the fibre as it passes through the pulling device. If the fibre is too weak, it breaks.

Prior art solutions are described e.g. in U.S. Pat. No. 4,601,208 and in JP publication 6129967.

A disadvantage of the prior art solutions is that they are hard to include in a continuous fibre manufacturing process because it has been difficult to continue the process after a fibre break without interfering with the pulling process.

The object of the invention is to provide a method and an apparatus which eliminate the disadvantages associated with the prior art. This is achieved with a method and apparatus according to the invention. The method of the invention is characterized in that in the case of a fibre break the fibre end is guided between the first and the second pulling device by means of a first channel section, which guides the fibre to the second pulling device, and that after the second pulling device the fibre end is guided to a second channel section which is off the normal fibre track and along which the fibre is guided into a scrap fibre processing system, and that at a desired moment the fibre is guided from the second channel section to the normal track, along which the fibre is guided onto a reel. The apparatus of the invention is characterized in that the apparatus comprises a first channel section which in the case of a fibre break is arranged to guide the fibre end between the first and the second pulling device to the second pulling device, a second channel section which is after the second pulling device off the normal fibre track and arranged to guide the fibre into a scrap fibre processing system, and transfer means which are arranged to guide the fibre at a desired moment from the second channel section to the normal track, which is arranged to guide the fibre onto a reel.

A major advantage of the solution according to the invention is that it allows combining of the proof testing with the fibre pulling process in an advantageous manner so that the fibre pulling process is not interfered with in any situation but can continue without interruptions at the maximal production rate. The reason for this is that the invention enables changeover of winding from one reel to another in an automatic double spooler even though fibre or a similar material to be wound would have broken or intentionally cut before the changeover of winding. A further advantage of the invention is that it allows winding of proof-tested fibre with a desired length onto a reel.

Figure 2:
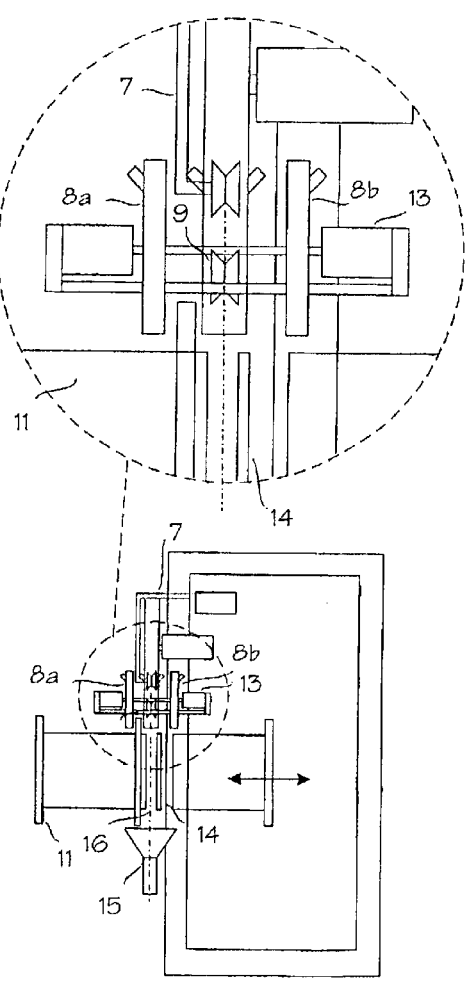
Figure 6:
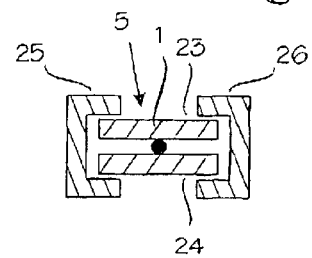
Figure 7:
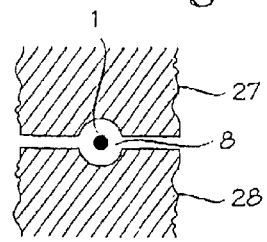
Figure 8:
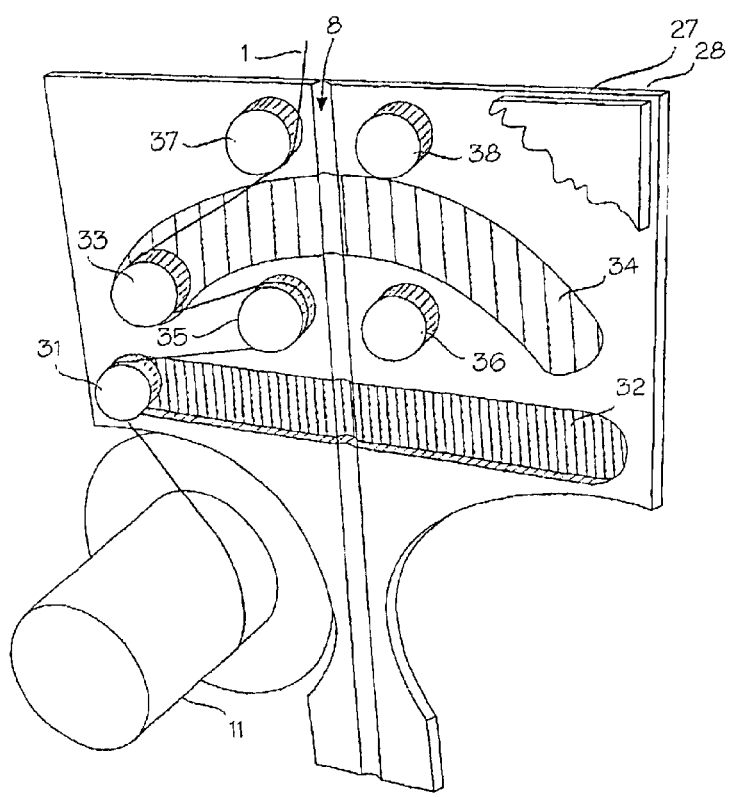

The invention will be described in greater detail by means of preferred embodiments shown in the accompanying drawing, in which FIG. 1 schematically illustrates a first embodiment of the apparatus according to the invention, FIG. 2 illustrates the embodiment of FIG. 1 from another direction, FIG. 3 schematically illustrates a second embodiment of the apparatus according to the invention, FIG. 4 illustrates the embodiment of FIG. 3 from another direction, FIG. 5 schematically illustrates a third embodiment of the apparatus according to the invention, FIG. 6 is a cross-sectional view of a detail of the embodiment shown in FIG. 5, FIG. 7 is a cross-sectional view of another detail of the embodiment shown in FIG. 5, and FIG. 8 is a perspective view of the embodiment of FIG. 5 from which part of the structure has been omitted for the sake of clarity.

FIGS. 1 and 2 schematically show a first embodiment of the apparatus according to the invention. In the figures reference number 1 denotes an optical fibre which enters the apparatus from a fibre pulling process. The fibre 1 direction is marked with an arrow in FIG. 1. Reference numbers 2 and 3 denote a first pulling device and a second pulling device. In the embodiment according to FIGS. 1 and 2 the first pulling device 2 is supported by guides so that the whole unit can move freely in the longitudinal direction of the fibre 1. However, the first pulling device 2 is pre-tightened against a power sensor 4 during installation, and thus in practice this unit is fixed. The idea of this embodiment is that in proof testing the fibre 1 pulls the whole unit forming the first pulling device 1 against the sensor 4, which then measures the tensile stress.

According to the invention, a first channel section 5, which in the embodiment shown in FIGS. 1 and 2 is made of a solid tubular member, is arranged between the first pulling device 2 and the second pulling device 3. If necessary, an ionised airflow can be led into the first channel section. In the case of a fibre break the first channel section 5 guides the fibre end into the opening of the second pulling device. The ends of the first channel section 5 are preferably shaped so that the fibre 1 cannot escape from between the end of the channel section and the second pulling device 3. The front end of the first channel section 5 can be provided with a cutter 6, which can be used for cutting the fibre 1 intentionally.

After the second pulling device 3 in the fibre 1 direction the apparatus comprises a unit which is provided with a dancer unit 7 functioning as fibre transfer means, a second channel section 8 and auxiliary wheels 9 and 10. During a normal run, the fibre moves from between the second pulling device 3 and the end of the second channel section 8 to the wheel of the dancer unit 7 and further onto a reel via the auxiliary wheel 9, or onto another reel 12 via the second auxiliary wheel 10, depending on the position of the dancer unit 7.

In the embodiment of FIGS. 1 and 2 the second channel section 8 is formed from an openable tubular section, which splits into two halves marked with reference numbers 8a and 8b in FIG. 2. The second channel section 8 can be opened and closed by means of a suitable opening mechanism 13.

During a normal run the second channel section 8 is closed, i.e. the halves 8a and 8b are against each other. If necessary, an ionised airflow can also be led into the second channel section 8.

As the fibre 1 breaks, its tail naturally travels onto the reel 11 via the dancer unit 7, for example. In this case the new fibre 1 end is guided inside the second channel section 8 and along it further towards a fibre gripping unit 14 and a suction device 15. From the suction device the fibre can be led into a scrap fibre processing system, for example. After the gripping unit 14 has caught the fibre 1 and winding has started, the second channel section 8 is opened and the wheel in the dancer unit moves to the other side of the channel section, taking the fibre to an auxiliary wheel on the same side and winding continues onto a reel 12 different from the one used before the break. Finally, the halves 8a and 8b of the second channel section 8 are pressed back together and the second channel section 8, which now is a tubular channel, remains waiting for a new fibre break. It should be noted that the fibre break may result from weakness of the fibre or can be caused by a cutter 6. The fibre is broken by the cutter 6 e.g. when fibres with the delivery length are run onto reels in a process which combines pulling and proof testing.

In the embodiment illustrated in FIGS. 1 and 2 the suction device 15 is arranged directly below the second channel section 8 so that the gripping unit 14 fits between them. When the gripping unit closes, a cutter 16 at its lower edge cuts off the fibre end towards the suction device. After the second channel section 8 has been opened and the fibre guided to the dancer unit, the spooler transfers it into the winding station. The reel in the second spooler is replaced with an empty reel, after which it can be transferred below the second channel section to wait for a fibre break. If there are a lot of fibre breaks, the clippings are usually led directly into the suction device 15.

FIGS. 3 and 4 illustrate a second embodiment of the apparatus according to the invention. The embodiment shown in FIGS. 3 and 4 corresponds to that of FIGS. 1 and 2 in several respects, and thus in FIGS. 3 and 4 the same reference numbers have the same significance as in FIGS. 1 and 2. FIG. 3 schematically illustrates an electric connection established between the first and the second pulling device 2 and 3. The electric connection is used to apply a desired amount of tensile stress to the fibre 1.

In the embodiment of FIGS. 3 and 4 the pulling devices 2 and 3, first channel section 5, dancer unit 7, auxiliary wheels 9 and 10, and second channel section 8 are arranged in the same way as in FIGS. 1 and 2. The embodiment of FIGS. 3 and 4 differs from that of FIGS. 1 and 2 in that in the former embodiment, there is a third pulling device, i.e. an auxiliary pulling device 17, and a second dancer unit 18 functioning as second fibre transfer means after the second channel section 8.

In principle, the function of the embodiment according to FIGS. 3 and 4 corresponds to that of the embodiment shown in FIGS. 1 and 2. In a normal situation the fibre travels in the embodiment illustrated in FIGS. 3 and 4 via the dancer unit 7 and the auxiliary wheel 9, for example, onto the reel 11. In the case of a fibre break the new fibre end travels via the first channel section 5 to the second pulling device and further to the auxiliary pulling device 17 along the second channel section. When the fibre 1 is attached to the auxiliary pulling device 17, the second channel section 8 is opened, and thus the second dancer unit 18 turns into the position shown with broken lines in FIG. 3, transferring the fibre close to the second reel 12, in which case the gripping unit can catch the fibre. Then the cutter 16 cuts it and winding continues onto the reel 12 as described above in connection with FIGS. 1 and 2. At the same time the dancer unit 7 transfers the fibre to the auxiliary wheel 10. Finally, the second channel section closes and remains waiting for a new fibre break. In this embodiment a discharge channel 19 leading to the suction device 15 is arranged after the auxiliary pulling device 17. The discharge channel can also be provided with a shredder which cuts the fibre to be disposed of.

FIGS. 5 to 8 illustrate a third embodiment of the invention. In FIGS. 5 to 8 the same reference numbers have the same significance as in FIGS. 1 to 4. In essence, the embodiment shown in FIGS. 5 to 8 corresponds to the embodiments described above; only some details are implemented differently from the preceding embodiments. In the embodiment shown in FIGS. 5 to 8 the first channel section 5 is formed using belts and pulleys and the second channel section 8 by means of two plate members that are arranged close to each other.

In the embodiment according to FIGS. 5 to 8 the tension related to the proof testing of fibre is generated by means of the rate and/or tension control of the first pulling device 2 and the second pulling device 3. Since one has to be able to manage the movements of the fibre end in the case of a fibre break, too, a tension measuring wheel cannot be used for tension measurement between the pulling devices. The force generated by the fibre in respect of the second pulling device can be measured e.g. by connecting the second pulling device 3 and its belts to suitable power sensors.

One feasible solution for controlling tension is a control where the first pulling device 2 functions as the master of line speed, rotating at a constant rate, or in the case of a drawing tower, as a pulling device that determines the pulling rate. In that case the second pulling device 3 is driven by a tension control controlled by power sensors.

A fibre break can be noticed e.g. by measuring the speed difference between the pulling devices 2, 3 with HW counters. By using pulse sensors in the motors of the pulling devices and by increasing the counter reading by the pulses of one pulling device and decreasing it by the pulses of the other one the counter will show the difference in length that corresponds to the fibre stretch. In connection with a fibre break this difference rapidly increases more than normally and the fibre break can be noticed. Furthermore, the difference in length resulting from the stretch and changes thereof can be utilized in calibration diagnostics of the power sensors. Other means for measuring a fibre break include the power sensor signal, motor current, etc.

In the embodiment of FIGS. 5 to 8 the pulleys of the pulling devices 2 and 3 are arranged so that the pulleys 21, 22 and the belts 23, 24 between them travelling in the same direction form a first channel section 5, which controls the movements of the fibre 1 during a fibre break and when the device is threaded. The first channel section 5 formed in the above-mentioned manner is shown in FIG. 6, which shows the channel section in the fibre 1 direction. By means of a suitable construction the length of the first channel section 5 can be made to cover nearly the whole length of the proof testing. Naturally it is also possible to use suitable nozzles which ensure that the fibre 1 is guided between the belts, etc. Guides 25, 26 shown in FIG. 6, which ensure that the fibre stays between the belts, can also be used between the pulleys 21, 22. The dimensions of the channel between the belts should be selected so that the fibre can move freely in the channel, in which case the tension applied to the fibre is generated only by the capstans of the pulling devices.

In the embodiment of FIGS. 5 to 8 the fibre 1 travels from the second pulling device 3 into a mechanism forming transfer means arranged to transfer the fibre to its normal track, to guide the fibre to the normal track during a normal run and to the second channel section 8 off from the normal fibre track. This mechanism consists of two plate-like members 27, 28 arranged against each other and related components. Between the plate-like members there is a narrow air gap, which may be e.g. 3 mm wide. The surfaces of the plate-like members are provided with grooves, and thus in this embodiment the plate-like members arranged against each other form a round-edged groove, which in this embodiment forms the second channel section 8, which can be seen e.g. in FIGS. 7 and 8. It should be noted that FIG. 8 shows only one of the plate-like members 28. For the sake of clarity, only a very small part of the other plate-like member 27 is shown in FIG. 8 since this allows a clearer illustration of the second channel section 8. The diameter of the second channel section may be 30 mm, for example. The second channel section 8 leads into a suction device 29, which is shown in FIG. 5.

When the suction device 29 is in use, it first generates an airflow from the front end of the second channel section 8 into the suction device and secondly an airflow from the sides of the plate-like members 27, 28 through the air gap along the whole length of the channel section first into the channel section and then into the suction device. If the size of the channel section and the air gap between the plate-like members are designed so that they are suitable for each other, it is possible to control how much of the airflow caused by the suction device comes into the channel section 8 from the end towards the second pulling device and how much of it comes from the air gap.

The arrangement described above enables use of the airflow caused by the suction device for guiding a fibre 1 that has broken during proof testing or has been intentionally cut into the suction device. Also in this embodiment the first channel section 5 can be provided with a cutter 30 for cutting the fibre intentionally.

FIGS. 5 to 8 further describe a construction by means of which the fibre can be deflected from the second channel section into the area of the air gap between the plate-like members 27, 28. This is utilized during the changeover and winding. In this embodiment it is also essential that even if the fibre had been deflected into the area of the air gap between the plate-like members 27, 28, the second channel section 8 remains functional without interruptions in case the fibre breaks during proof testing. This is useful particularly when proof testing is included in fibre pulling. In that case it may happen that the fibre is very weak for some time and several fibre breaks occur one after another.

In this embodiment the fibre transfer means include a transfer wheel 31 which is arranged to move in a groove 32 formed by the plate-like members 27, 28, e.g. linearly from one side to the other. The width of the transfer wheel 31 is chosen so that it reliably takes along the fibre 1 travelling in the second channel section 8. The transfer means further comprise an accumulator wheel 33, which moves e.g. along a circular track in the groove 34 from one side to the other. The width of the collected wheel 33 is also chosen so that it reliably takes along the fibre 1 travelling in the second channel section 8. The transfer means also comprise fixed control wheels 35 to 38 which are embedded in the cavities included in the plate-like members 27, 28 so that when the transfer wheel 31 or the accumulator wheel 33 deflects the fibre from the second channel section 8, it is guided reliably and correctly.

In principle, the embodiment according to FIGS. 5 to 8 functions as follows. It is assumed that in the initial situation the fibre travels along the second channel section 8 into the suction device, e.g. when the run starts. When winding is to be started, the transfer wheel 31 moves across the second channel section 8 to the opposite side, deflecting the fibre 1 so that it travels from the transfer wheel into the suction device along a track which guides the fibre between the gripping flange of the gripping mechanism. The principles of the gripping mechanism were described in connection with FIGS. 1 to 4. Immediately before the gripping flange is activated, the accumulator wheel 33 also moves to the same edge as the transfer wheel and winding of the fibre onto the reel 11 begins as shown in FIG. 8.

If the fibre breaks after the phase described above during the proof testing, the airflow generated by the suction device 29 takes the free end of the fibre along the second channel section 8 into the suction device, after which changeover of winding onto a new reel can be performed at a desired moment as described above, i.e. by moving the transfer wheel 31 and the accumulator wheel 33 to the opposite side, i.e. to the side of the new reel.

If the fibre 1 is still weak when it is guided between the gripping flanges of the gripping mechanism, this will cause no problems because the second channel section 8 is ready to function all the time and takes any broken fibres into the suction device. Since the changeover is a critical point in respect of the fibre strength, the above-mentioned fact significantly improves the reliability of the apparatus.

If the fibre should be transferable onto a new reel at any desired moment, the apparatus must include a fibre cutter for cutting the fibre. In the embodiment of FIGS. 5 to 8 a fibre cutter 30 is arranged between a construction comprising the second pulling device 3 and the plate-like members 27, 28. After the fibre has been cut by the cutter 30, it is guided onto a new reel as described above. The fibre cutter can be used also when the accumulator wheel and/or the transfer wheel are on the wrong side of the second channel section with respect to the reel onto which the fibre is to be guided. In that case the cutter causes an additional fibre break after the accumulator wheel/transfer wheel has been moved into the initial position required by the changeover. After the break the fibre automatically moves into the channel, and thus the changeover can be performed as usual.

The embodiments described above are by no means intended to limit the invention, but the invention may be modified freely within the claims. It is thus clear that the apparatus of the invention or its details need not exactly correspond to those shown in the figures, but other solutions are also possible. For example, the second channel section can also be formed by two belt sections as shown in FIG. 6, etc. In an embodiment like this the controllers at the edges of the belts can be parts that that turn sideways.

What is claimed is:

1. A proof testing method for optical fibre where a fibre is guided in a direction of motion to a first pulling device and further to a second pulling device and then onto a reel, whereby the pulling devices subject the fibre to a desired amount of tensile stress, as a result of which the fibre breaks if a strength of the fibre is insufficient, and in which method in the case of a fibre break a first fibre end positioned after the break relative to the direction of motion is guided between the first and the second pulling device by a first channel section, which guides the first fibre end to the second pulling device, and after the second pulling device the first fibre end is guided into a second channel section which is off a normal fibre track and along which the first fibre end is guided into a scrap fibre processing system, and at a desired moment the fibre with the first fibre end is cut and a second fibre end positioned after the cut relative to the direction of motion is guided to the normal track, along which the second fibre end is guided onto a reel.

2. A method according to claim 1, wherein the second fibre end positioned after the cut is guided onto a different reel than a fibre end positioned before the fibre break.

3. A proof testing apparatus for optical fibre, the apparatus comprising a first pulling device and a second pulling device and a winding device, the pulling devices being arranged to subject a fibre to a desired amount of tensile stress which makes the fibre break if a strength of the fibre is insufficient, wherein the apparatus further comprises a first channel section which in the case of a fibre break is arranged to guide a first fibre end positioned after the break relative to a direction of motion between the first and the second pulling device to the second pulling device, a second channel section which is after the second pulling device off the normal fibre track and arranged to guide the first fibre end into a scrap fibre processing system, a first cutter to cut the fibre with the first fibre end at a first desired moment and a transfer device which is arranged to guide a second fibre end positioned after the cut relative to the direction of motion to the normal track, which is arranged to guide the second fibre end onto a reel.

4. An apparatus according to claim 3, wherein the transfer device is arranged to guide the second fibre end positioned after the cut to a different reel than a fibre end positioned before the break.

5. An apparatus according to claim 3, wherein the first channel section is formed of a tubular member.

6. An apparatus according to claim 3, wherein the first channel section is arranged to comprise two adjacent belts.

7. An apparatus according to claim 3, wherein the second channel section is made of a tubular member which is openable in the longitudinal direction.

8. An apparatus according to claim 3, wherein the second channel section is formed by two plate-like members which are close to each other.

9. An apparatus according to claim 3, wherein the second channel section is formed of two belts.

10. An apparatus according to claim 3, wherein the first channel section is provided with a second cutter for cutting the fibre at a second desired moment.

11. A method for proof testing a fibre, the method comprising:
    placing the fibre in motion in a direction of motion;
    subjecting the fibre to a desired amount of stress while the fibre remains in motion;
    cutting the fibre while the fibre remains in motion resulting in a first fibre end after a first cut relative to the direction of motion; and
    guiding the first fibre end to a first reel while the fibre remains in motion.

12. The method of claim 11, wherein a fibre end positioned before the fibre cut relative to the direction of motion is guided onto a second reel.

13. The method of claim 11, wherein upon a break occurring in the fibre as a result of applying the desired amount of stress, the method further comprises:
    guiding a second fibre end positioned after the break relative to the direction of motion to a scrap container while the fibre remains in motion;
    directing a portion of the fibre connected to the second fibre end to the scrap container;
    cutting the fibre connected to the second fibre end while the fibre remains in motion, resulting in a third fibre end positioned after a second cut relative to the direction of motion; and
    guiding the fibre connected to the third fibre end to a second reel while the fibre remains in motion.

14. An apparatus for proof testing a fibre, comprising:
    a first pulling device and a second pulling device that subject the fibre to a desired amount of stress while the fibre remains in motion in a direction of motion;
    a first channel that guides the fibre between the first pulling device and the second pulling device;
    a first cutter, positioned between the first and second pulling devices, that cuts the fibre while the fibre remains in motion resulting in a first fibre end after a first cut relative to the direction of motion; and
    a transfer device that guides the first fibre end from the second pulling device to a first reel while the fibre remains in motion.

15. The apparatus of claim 14, wherein the transfer device is configured to guide a fibre end positioned before the fibre cut relative to the direction of motion onto a second reel.

16. The apparatus of claim 14, further comprising:
    a second channel to guide, upon a break occurring in the fibre as a result of applying the desired amount of stress, a second fibre end positioned after the break relative to the direction of motion to a scrap container while the fibre remains in motion; and
    a second cutter positioned between the second channel and the scrap container that cuts the fibre connected to the second fibre end while the fibre remains in motion in a direction of motion, resulting in a third fibre end positioned after a second cut relative to the direction of motion;
    wherein the transfer device is configured to guide the third fibre end to a second reel while the fibre remains in motion.

* * * * *